(12) United States Patent
Antoine et al.

(10) Patent No.: US 7,981,856 B2
(45) Date of Patent: *Jul. 19, 2011

(54) SURFACTANT COMPOSITION METHOD FOR PRODUCTION THEREOF AND COSMETIC COMPRISING SAID COMPOSITION

(75) Inventors: Jean-Pierre Antoine, Francheville (FR); Jerome Marcilloux, Saint Symphorien d'Ozon (FR); Martine Lefeuvre, Thorigne-Foulliard (FR); Daniel Plusquellec, Noyal Chatillon sur Seiche (FR); Thierry Benvegnu, Rennes (FR); Fabrice Goursaud, Esvres sur Indre (FR); Bernard Parant, Ozoir la Ferriere (FR)

(73) Assignees: Eiffage Travaux Publics, Neuilly sur Marne (FR); Ecole Nationale Superieure de Chimie de Rennes, Rennes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/769,698

(22) Filed: Apr. 29, 2010

(65) Prior Publication Data

US 2010/0273694 A1 Oct. 28, 2010

Related U.S. Application Data

(62) Division of application No. 11/579,592, filed as application No. PCT/FR2005/001103 on May 3, 2005, now Pat. No. 7,829,521.

(30) Foreign Application Priority Data

May 4, 2004 (FR) ..................................... 04 04757

(51) Int. Cl.
 *B05D 5/00* (2006.01)
(52) U.S. Cl. ........................................ 510/506; 510/499
(58) Field of Classification Search .................. 510/499, 510/506
 See application file for complete search history.

(56) References Cited

U.S. PATENT DOCUMENTS

| | | | |
|---|---|---|---|
| 2,888,383 A | | 5/1959 | Byrne |
| 3,422,026 A | * | 1/1969 | Wright ............................ 516/45 |
| 4,294,728 A | * | 10/1981 | Vanlerberghe et al. ....... 510/119 |
| 5,961,999 A | * | 10/1999 | Bimczok et al. ............... 424/401 |
| 6,329,483 B1 | * | 12/2001 | Schade et al. .................. 526/263 |
| 6,384,266 B1 | | 5/2002 | Farone et al. |
| 2007/0243321 A1 | | 10/2007 | Antoine et al. |

FOREIGN PATENT DOCUMENTS

| | | |
|---|---|---|
| DE | 35 27 974 | 2/1987 |
| EP | 0 750 904 | 1/1997 |
| EP | 1 016 650 | 7/2000 |
| JP | 49 076 818 | 7/1974 |

* cited by examiner

*Primary Examiner* — Milton I Cano
*Assistant Examiner* — M. Reza Asdjodi
(74) *Attorney, Agent, or Firm* — Oblon, Spivak, McClelland, Maier & Neustadt, L.L.P.

(57) ABSTRACT

The invention relates to surfactant compositions made from esters or amides of the betaine glycine, produced by reaction of the glycine betaine with a sulphonic acid and an alcohol or a fatty-chain amine derived from vegetable oils. The invention further relates to a cosmetic comprising said surfactant composition, in particular, liquid soap, bath foam, shower gel or shampoo.

21 Claims, 1 Drawing Sheet

SURFACTANT COMPOSITION METHOD FOR PRODUCTION THEREOF AND COSMETIC COMPRISING SAID COMPOSITION

REFERENCE TO PRIOR APPLICATIONS

This application is a Divisional of U.S. application Ser. No. 11/579,592, filed Jan. 4, 2007, now U.S. Pat. No. 7,829,521; which is a 371 application of PCT/FR05/01103, filed May 3, 2005; claims priority to French patent application 04 04757, filed May 4, 2004, all incorporated herein by reference.

This invention was made under a joint research agreement between Eiffage Travaux Publics of Neuilly sur Marne, France and Ecole Nationale Supérieure de Chimie Rennes of Rennes, France.

FIELD OF THE INVENTION

The invention relates to surfactant compositions.

BACKGROUND OF THE INVENTION

From detergents to cosmetic formulations, via emulsification, the chemistry of surfactants supplies an extremely varied range of products which are nowadays indispensable to our daily life. Although the market for cationic amphiphiles is quantitatively smaller than that for anionic or non-ionic amphiphiles, representing a percentage of the worldwide production of less than 10%, it is nevertheless very extensive and covers numerous applications.

Due to their toxicity, certain surfactants such as the salts of dimethyldialkyl ammonium which are present in most textile conditioners, are restricted in use, and have even been abandoned in some European countries such as Germany and the Netherlands. Under the pressure of environmental considerations, the manufacturers of surfactants are having to propose not only methods compatible with these new requirements, but also less polluting products which are more biodegradable and cause the lowest possible pollution of the environment. Added to the environmental constraints is a considerable commercial argument, of using what is "natural". To respond to the demands of the consumer, and at pains to find products having a "green image", the manufacturers are currently researching new structures and are naturally turning to the use of raw materials of agricultural origin.

If, for the lipophilic part of these molecules, competition is well established between the petrochemical substances and the oleochemical substances, it is not yet really engaged as far as the hydrophilic part of these molecules is concerned. The direct use of natural triglycerides, such as triglycerol ricinoleate [U.S. Pat. No. 4,857,310 (The Gillette Company)], makes it possible to have easy access to cationic amphiphilic compounds. But the diversification of the structures is effected also by modification of the polar head. Cationic surfactants, derived in particular from glucuronic acid and galacturonic acid [DE 195 39 845 (Henkel KgaA)] or with a starch base comprising a sugar entity derived from alkyl polyglycosides (APG) [WO 90 15809 (Henkel KgaA)] have been proposed. Another type of surfactant is appearing. This involves molecules having a saponifiable ester function between the fatty chain and the quaternary ammonium function, such as ammonium chlorides [U.S. Pat. No. 5,527,477 (Lever Brothers Company)]. Being easily hydrolysable, the betaine esters are also currently stirring up strong interest. Various derivatives have been synthesised ([WO 96 09276 (The Procter and Gamble Company:], [U.S. Pat. No. 5,527, 477 (Lever Brothers Company)], intended for applications such as textile conditioners.

Betaine glycine, a cheap natural substance, forms a raw material of choice for the production of surfactant agents. Representing 27% by weight of sugar-beet molasses, obtained after extraction of the sucrose, it remains currently a by-product of the sugar industry. The grafting on to the betaine glycine of fatty alcohols and fatty acids ([U.S. Pat. No. 2,888,383 (International Minerals and Chemical Corporation)], [EP 0 750 904 A1 (Wella-AG)] makes it possible to obtain amphiphilic cationic molecules without the conventional stage of quaternisation of a tertiary amine using methylation agents which are generally toxic.

BRIEF DESCRIPTION OF THE DRAWINGS

SUMMARY OF THE INVENTION

The present invention aims to propose means of rapidly obtaining mixtures of a perfectly defined composition with a base of esters or amides of the betaine glycine obtained in the form of reactional raw materials or by washing of the reactional raw materials with organic solvents. The methods of synthesis used are simple, efficient, respect the environment without solvent or pollutant waste, are easy to convert on an industrial scale and allow the upgrading of a by-product of the sugar industry and of vegetable oils of domestic origin (e.g. colza or sunflower) which are rich in fatty chains with a high carbon condensation (stearic, oleic, linoleic, linolenic, arachidic, gadolic, behenic, erucic chains) which are even less re-used compared to oleaginous resources of tropical origin (e.g. palm, cabbage tree or copra) which are rich in caprylic, capric, lauric, myristic or palmitic chains.

The 18-atom fatty chains of carbons derived from domestic vegetable oils are known for their emulsifying properties and the compositions according to the invention cover a large range of potential applications in the field of emulsification, as well as in the petrol industry, the mining industry, the paint, pigment and varnish industry or in the building and civil engineering industry.

The invention also relates to the use of the mixtures mentioned above by way of detergent, emulsifying or foaming agents for applications in the cosmetics field.

BRIEF DESCRIPTION OF THE DRAWING

The only drawing shows the results obtained for the stability of octadecyl betaine mesylate in an aqueous buffer solution whose pH-value is fixed to various values between 3 and 9.

DETAILED DESCRIPTION OF THE PREFERRED EMBODIMENTS

The invention relates in particular to a surfactant composition comprising: at least one compound of formula (1)

$$X^-(CH_3)_3N^+-CH_2-CO-Z-R \quad (1)$$

and at least one compound selected from those with formulae (2), (3) and (4)

$$RZH \quad (2)$$

$$XH \quad (3)$$

$$X^-(CH_3)_3N^+-CH_2-CO-OH \quad (4)$$

X being a sulphonate radical,

R being a monovalent radical of formula $C_{2n}H_{2(2n-m)+1}$ containing 2n atoms of carbon and m double bonds, with $9 \leq n \leq 11$, $0 \leq m \leq 3$ if n=9 and $0 \leq m \leq 1$ if n>9, and Z being selected from an atom of oxygen and a —NH— group, a compound of formula XH being combined if necessary with at least one compound of formula $RNH_2$ in order to form at least one compound of formula $X^-RN^+H_3$.

Advantageously, the composition according to the invention comprises virtually exclusively compounds of the said formulae (1), (2), (3) and (4).

Optional additional or alternative features of the invention are indicated below:

m=0 and the compounds forming the composition are as follows, in the percentages by weight indicated:

| | |
|---|---|
| $X^-(CH_3)_3N^+$—$CH_2$—CO—O—R | 50 ± 10 |
| ROH | 19 ± 10 |
| XH | 23 ± 10 |
| $X^-(CH_3)_3N^+$—$CH_2$—CO—OH | 0 to 18. | m=0 and the compounds forming the composition are the following, in the percentages by weight indicated:

| | |
|---|---|
| $X^-(CH_3)_3N^+$—$CH_2$—CO—O—R | 72 ± 10 |
| ROH | 0 to 20 |
| XH | 0 to 18 |
| $X^-(CH_3)_3N^+$—$CH_2$—CO—OH | 0 to 20 | m=0 and the compounds forming the composition are the following, in the percentages by weight indicated:

| | |
|---|---|
| $X^-(CH_3)_3N^+$—$CH_2$—CO—O—R | 80 ± 10 |
| ROH | 20 ± 10. | m=0 and the compounds forming the composition are the following, in the percentages by weight indicated:

| | |
|---|---|
| $X^-(CH_3)_3N^+$—$CH_2$—CO—O—R | 70 ± 10 |
| ROH | 26 ± 10 |
| XH | 0 to 14. | m>0 and the compounds forming the composition are the following, in the percentages by weight indicated:

| | |
|---|---|
| $X^-(CH_3)_3N^+$—$CH_2$—CO—O—R | 48 ± 10 |
| ROH | 36 ± 10 |
| XH | 14 ± 10 |
| $X^-(CH_3)_3N^+$—$CH_2$—CO—OH | 0 to 12. | m=0 and the compounds forming the composition are the following, in the percentages by weight indicated:

| | |
|---|---|
| $X^-(CH_3)_3N^+$—$CH_2$—CO—NH—R | 58 ± 10 |
| $X^-RN^+H_3$ | 35 ± 10 |
| $X^-(CH_3)_3N^+$—$CH_2$—CO—OH | 0 to 20. | m>0 and the compounds forming the composition are the following, in the percentages by weight indicated:

| | |
|---|---|
| $X^-(CH_3)_3N^+$—$CH_2$—CO—NH—R | 56 ± 10 |
| $X^-RN^+H_3$ | 31 ± 10 |
| $RNH_2$ | 0 to 18 |
| $X^-(CH_3)_3N^+$—$CH_2$—CO—OH | 0 to 15. |

X is selected from the radicals methanesulphonate, paratoluenesulphonate and camphorsulphonate.

The invention also has the object of a method of preparing a composition such as defined above in which betaine glycine is reacted with a sulphonic acid and a compound of the formula ROH in the absence of other solvents, the molar ratio of the sulphonic acid to betaine glycine being comprised between 2 and 3 and the molar ratio of the compound ROH to betaine glycine being between 1 and 1.5.

The method according to the invention may comprise at least some of the following features:

The reaction is carried out at a temperature of between 130 and 140° C. for 6 to 8 hours.

The reaction is carried out under reduced pressure, preferably of between 50 and 100 mbar.

m=0 and the reactional mixture is treated with an organic solvent capable of dissolving preferably the compounds other than the $X^-(CH_3)_3N^+$—$CH_2$—CO—O—R contained therein so as to obtain a precipitate enriched in $X^-(CH_3)_3N^+$—$CH_2$—CO—O—R.

the organic solvent is selected from diethyl ether, ethanol and n-butanol.

The betaine glycine is reacted with a sulphonic acid and the n-butanol in the absence of other solvents, the molar ratio of the sulphonic acid to the betaine glycine being between 1 and 1.3 and the molar ratio of the n-butanol to the betaine glycine between 2 and 4 in order to form water and the n-butylic ester sulphonate of betaine glycine which is reacted—after having eliminated the water and the n-butanol—with the compound of formula $RNH_3$, the molar ratio of this compound to the betaine glycine being between 1 and 1.2.

The reaction of the betaine glycine with the sulphonic acid and the n-butanol is carried out at a temperature of between 130 and 140° C., upon reflux of the n-butanol, for 3 to 5 hours under atmospheric pressure so as to realise azeotropic elimination of water.

Before the compound of formula $RNH_2$ is added, a strong encumbered organic base is added, in particular dibutylamine, the molar ratio of the said base to the betaine glycine being between 0.1 and 0.4.

m=0 and the reactional mixture is treated with an organic solvent capable of dissolving preferably the compound $RNH_2$ so as to obtain a precipitate enriched with $X^-(CH_3)_3N^+$—$CH_2$—CO—NH—R.

The organic solvent is diethyl ether.

The sulphonic acid is selected from methanesulphonic, paratoluenesulphonic and camphorsulphonic acid.

The invention also aims at a cosmetic, in particular a liquid soap, bath foam, shower gel or shampoo and in particular acid shampoo, comprising from 0.2 to 60% and preferably from 10 to 45% by weight of a composition such as defined above and from 99.8 to 40% and preferably from 90 to 55% by weight of excipients appropriate for cosmetology.

Advantageously in the cosmetic according to the invention, the excipients are selected from thickeners, texturisers, conditioning agents, softeners, complexing agents, perfumes, pearlising agents, preservatives, acidifiers and purified water, and comprise as texturisers diethylanolamides of fatty acids, in particular diethanolamide of copra, with a content not exceeding 10% by weight of the cosmetic.

A first type of composition according to the invention has a base of fatty esters of the betaine glycine.

The method of preparing these mixtures consists in reacting the betaine glycine with 2 to 3 molar equivalents of a sulphonic acid and 1 to 1.5 molar equivalent of a saturated fatty alcohol of the type $C_{18:0}$, $C_{20:0}$ or $C_{22:0}$ or of a non-saturated fatty alcohol of the type $C_{18:1}$, $C_{18:2}$, $C_{18:3}$, $C_{20:1}$ or $C_{22:1}$, the numbers before and after the sign ":" representing respectively the number of carbon atoms and the number of double carbon-carbon bonds. The esterification reaction of the betaine glycine in the zwitterionic form requires previous protonation of its carboxylate function. The acid of the betaine reacts with the fatty alcohol in the presence of the excess of acid in order to lead to the corresponding esters. This reaction is carried out in the absence of any solvent, the fatty alcohol used forming both the reagent and the medium.

Preferably, the reaction is carried out at a temperature of between 130 and 140° C. for 6 to 8 hours. The water formed during the reaction is eliminated continuously under reduced pressure, preferably of between 50 and 100 mbar.

The reactional raw materials resulting from carrying out of the method described make it possible to obtain mixtures formed of fatty ester of the betaine glycine, residual fatty alcohol, residual sulphonic acid and residual betaine glycine present in the protonated form, these constituents having the coefficients a, b, c and d respectively, the values of which can be determined by spectroscopy of RMN $^1$H.

When a saturated fatty alcohol is used in the reaction, rapid partial purification based on the difference of solubility between the fatty alcohol and the synthesised ester consists in the recovery of the reactional raw material by means of organic solvents such as diethyl ether, ethanol or n-butanol at the end of the reaction. The ester, insoluble in solvents such as diethyl ether or ethanol or partially soluble in butanol, precipitates and the fatty alcohol partially dissolves. By filtration, powders are obtained which are mainly formed of ester whose composition by mass may be determined by spectroscopy of RMN $^1$H.

According to the organic solvent used to wash the reactional raw materials, the coefficients a, b, c and d vary. The use of alcohols with short carbon chains makes it possible to obtain mixtures where the coefficients c and d are roughly equal to zero, the use of diethyl ether makes it possible to obtain mixtures having a low residual rate of saturated fatty alcohol (b). The excellent solubility of non-saturated fatty alcohols and of their corresponding esters in organic solvents does not make it possible to apply the method described, and the only ones that can be obtained are mixtures in the form of reactional raw materials.

It is possible to purify fatty esters of betaine glycine by chromatography of the mixtures according to the invention on a column of silica gel by means of ternary polar eluants of the type ethyl acetate/isopropanol/water.

The fatty esters of betaine glycine have a hydrolysable function between the fatty chain and the quaternary ammonium. The study of their behaviour in an aqueous medium makes it possible to contribute an important fact concerning their biodegradability. The stability of the derivatives is tested by chromatography in a gaseous phase by metering the fatty alcohol produced during the hydrolysis reaction in an aqueous buffer solution whose pH-value is fixed at different values.

The measurement of the surface tensions and critical micellar concentrations proves that the synthesised derivatives have amphiphilic properties which make it possible to use the mixtures proposed as surfactant agents (in particular as emulsifiers).

The other family of mixtures according to the invention has a base of fatty amide of betaine glycine.

The method of preparing these mixtures in the first instance uses the reaction of the betaine glycine with 1 to 1.3 molar equivalent of a sulphonic acid and 2 to 4 molar equivalents of n-butanol forming both the reagent and the medium in order to form the n-butyl ester in the form of intermediate sulphonate. Preferably, the first stage is carried out at a temperature of between 130 and 140° C., at the reflux of the n-butanol, for 3 to 5 hours and at atmospheric pressure. The slow distillation of the n-butanol makes it possible to eliminate azeotropically the water formed during the reaction. To the mixture cooled to ambient temperature is then added 1 to 1.2 molar equivalent of a saturated fatty amine of the type $C_{18:0}$, $C_{20:0}$ or $C_{22:0}$ or of a non-saturated fatty amine of the type $C_{18:1}$, $C_{18:2}$, $C_{18:3}$, $C_{20:1}$ or $C_{22:1}$. The reactional medium is heated under reduced pressure to eliminate the n-butanol and aminolysis is carried out for 2 to 4 hours at 130° C. between 50 and 100 mbar.

The formation of the salt of fatty amine resulting from the protonation of the amine by the excess of acid can be limited by the use of 0.1 to 0.4 molar equivalent of a strong, encumbered organic base such as dibutylamine added before the fatty amine.

The reactional raw materials resulting from carrying out the method described make it possible to obtain mixtures formed of fatty amide of betaine glycine, sulphonate of the fatty amine used during aminolysis, a low residue of fatty acid and of residual betaine glycine present in a protonated form, these constituents having coefficients e, f, g and h respectively, the values of which can be determined by spectroscopy of RMN $^1$H.

When a saturated fatty amine is used in the reaction, rapid partial purification based on the difference of solubility between the fatty amine and the synthesised amide consists in the recovery of the reactional raw material by means of diethyl ether at the end of the reaction. The amide and the salt of the fatty amine which are insoluble in the solvent precipitate and the fatty amine dissolves. By filtration, powders are obtained which are mainly formed of amide whose composition by mass can be determined by spectroscopy of RMN $^1$H. The use of diethyl ether makes it possible to obtain mixtures having a residual proportion of saturated fatty amine (g) roughly equal to zero. The recovery of the reactional raw materials by means of alcohols with short carbon chains such as ethanol or n-butanol leads to dissolving of the residues.

The excellent solubility of non-saturated fatty amines and of the corresponding amides in organic solvents does not make it possible to apply the method described and the only ones obtainable are mixtures in the form of reactional raw materials.

The fatty amides of the betaine glycine can be purified by chromatography of the mixtures according to the invention on a column of silica gel by means of ternary polar eluants of the type ethyl acetate/isopropanol/water.

The measurement of the surface tensions and critical micellar concentrations proves that the synthesised amide derivatives also have amphiphilic properties which make it possible to use the mixtures proposed as surfactant agents (in particular as emulsifiers).

The ester and amide derivatives of the betaine glycine have good surfactant properties with surface tensions and critical micellar concentrations which are relatively low. These derivatives according to the invention have surface tensions of the same order as the reference surfactants such as alkyl polyglucosides or sodium dodecyl sulphate (known by the registered Trade Mark SDS), which is widely used in industry. Compared to these commercial derivatives, critical micellar concentrations are obtained which are lower, which has a major advantage. In fact, less product is needed to obtain micellar solutions.

In the presence of water, these derivatives hydrate to varying degrees according to the condensation of carbon in the chains. They thus make it possible to homogenise a water-oil mixture by acting on the interactions which are both hydrophilic (surfactant/water) and lipophilic (surfactant/oil). They allow the formulation of very stable emulsions, including for low concentrations of surfactant, for variable water/surfactant/oil ratios and for different types of oil (in particular fatty acid methyl esters).

These single-chain surfactants are found to be very advantageous due to their foaming capacity and the stability of the foams formed, since they are as effective as SDS (registered Trade Mark), hence their use in the formulation of foaming products such as shampoos, liquid soaps, shower gels and bath foams.

Thus, the invention supplies cosmetics containing 0.2 to 60% and preferably 10 to 45% by weight of a surfactant composition according to the invention and from 99.8 to 40% and preferably 90 to 55% by weight excipients.

Such a cosmetic may be a liquid soap, a bath foam, a shower gel or a shampoo, in particular an acid shampoo having excellent foaming properties, associated with excellent volumising properties, giving body to the user's hair. An acid shampoo is for example composed of 10 to 45% by weight of a surfactant composition according to the invention with a base of fatty esters of the betaine glycine and 90 to 55% additives. The additives may be thickeners, texturisers, such as diethanolamide of fatty acids, in particular diethanolamide of copra which is incorporated at a level of 0-10% by weight in the formulation, conditioning agents, softeners, complexing agents and finally perfumes, pearlising agents, preservatives, acidifiers in sufficient quantity, and purified water.

The invention is further illustrated by the following examples.

EXAMPLE 1

Synthesis of Octadecyl Betaine Mesylate and Preparation of the Corresponding Mixtures To a suspension of betaine glycine (25 g, 0.213 mole) in methanesulphonic acid (53.3. g, 0.555 mole) is added octadecanol (69.3 g, 0.256 mole). The mixture thus obtained is heated progressively to 130° C. under reduced pressure (50 to 60 mbar) to eliminate the water formed during the esterification reaction. The mixture becomes homogeneous at the end of 1 to 2 hours' stirring at the same temperature. After 7 hours, the medium is cooled to ambient temperature.

Method A: The reactional raw material obtained (143 g) forms a first composition according to the invention.

Method B: The reactional raw material obtained is washed with diethyl ether (600 ml) until complete recovery of the residue. The precipitate obtained is then filtered on Büchner and rinsed several times with the same solvent (2 □.200 ml). The product is dried in a vacuum and 96 g of a white powder is eventually obtained.

Method C: The reactional raw material obtained is washed with ethanol (800 ml) until complete recovery of the residue. The precipitate obtained is then filtered on Büchner and rinsed several times with the same solvent (2 □.200 ml). The product is dried in a vacuum and 87 g of a white powder is eventually obtained.

Method D: The reactional raw material obtained is washed with n-butanol (900 ml) until complete recovery of the residue. The precipitate obtained is then filtered on Büchner and rinsed several times with the same solvent (2 □.200 ml). The product is dried in a vacuum and 42 g of a slightly grey powder is eventually obtained.

The composition of each mixture is evaluated by RMN of the proton by measuring the integration ratios between the different components. The RMN spectra are recorded on a Bruker ARX-400 apparatus. The RMN $^1$H spectra are obtained at 400 MHz (s=singlet, d=doublet, t=triplet, m=multiplet, I=wide). The RMN $^{13}$C spectra are obtained at 100 MHz in the decoupling mode of the proton. The chemical displacements are given in ppm relative to internal TMS ($\delta$ scale) and the coupling constants (J) in Hz.

RMN $^1$H of the reactional raw material (CDCl$_3$+CD$_3$OD, 1/1):

$\delta$ 0.84 (t, CH$_3$ ester +CH$_3$ alcohol, $^3$J 6.7 Hz), 1.22 (sl, (CH$_2$)$_{15}$CH$_3$ ester +(CH$_2$)$_{15}$CH$_3$ alcohol), 1.51 (m, CH$_2$CH$_2$O alcohol), 1.65 (m, CH$_2$CH$_2$O ester), 2.73 (s, CH$_3$SO$_3^-$ ester +CH$_3$SO$_3^-$ acid+CH$_3$SO$_3^-$ betaine glycine), 3.29 (s, (CH$_3$)$_3$ ester +(CH$_3$)$_3$ betaine glycine), 3.51 (t, CH$_2$CH$_2$O alcohol, $^3$J 6.7 Hz), 4.20 (t, CH$_2$CH$_2$O ester, $^3$J 6.8 Hz), 4.25 (s, CH$_2$CO betaine glycine), 4.33 (s, CH$_2$CO ester).

Composition of the Mixtures

| Method of treatment | a | b | c | d |
|---|---|---|---|---|
| A | 50 | 19 | 23 | 8 |
| B | 72 | 10 | 8 | 10 |
| C | 80 | 20 | 0 | 0 |
| D | 70 | 26 | 4 | 0 | a, b, c and d are expressed as a percentage by mass.

The reactional raw material or the product obtained by the method of treatment B is chromatographed on a column of silica gel (ethyl acetate-isopropanol-water (6.2:3:0.8)) in order to give about 70 g of octadecyl betaine mesylate.

C$_{24}$H$_{51}$NO$_5$S; M=465.74 g/mole
White solid; yield: ≈70%
CCM: Rf 0.39 (ethyl acetate-isopropanol-water (6:3:1))
IR (Nujol) ν (cm$^{-1}$): 1755 (C=O)
RMN $^1$H(CDCl$_3$+CD$_3$OD, 1/1):

$\delta$ 0.83 (t, 3H, CH$_3$, $^3$J 6/7 Hz), 1.22 (sl, 30H, (CH$_2$)$_{15}$CH$_3$), 1.65 (m, 2H, CH$_2$CH$_2$O), 2.70 (s, 3H, CH$_3$SO$_3^-$), 3.29 (s, 9H, (CH$_3$)$_3$), 4.20 (t, 2H, CH$_2$CH$_2$O, $^3$J 6.7 Hz), 4.34 (s, 2H, CH$_2$CO).

RMN $^{13}$C(CDCl$_3$+CD$_3$OD, 1/1):

$\delta$ 14.33 (CH$_3$), 23.17, 26.22, 28.82, 29.71, 29.88, 30.02, 30.08, 30.19, 32.45 (CH$_2$ aliph.), 39.50 (CH$_3$SO$_3^-$), 54.18 ((CH$_3$)$_3$), 63.46 (CH$_2$CH$_2$O), 67.27 (CH$_2$CO) 165.24 (CH$_2$CO).

EXAMPLE 2

Synthesis of 9-octadecenyl Betaine Mesylate and Preparation of the Corresponding Mixture To a suspension of betaine glycine (30 g, 0.256 mole) in methanesulphonic acid (61.523 g, 0.64 mole) is added oleic alcohol (96.25 g, 0.359 mole). The mixture thus obtained is heated progressively to 130° C. under reduced pressure (50 to 100 mbar) in order to eliminate the water formed during the esterification reaction. The mixture becomes homogeneous at the end of 1 to 2 hours' stirring at the same temperature. After 7 hours, the medium is cooled to ambient temperature. The reactional raw material obtained (210 g) forms a composition according to the invention.

RMN $^1$H of the reactional raw material (CDCL$_3$):

δ 0.83 (t, CH$_3$ ester +CH$_3$ alcohol, $^3$J 6.8 Hz), 1.22 (sl, CH$_3$(CH$_2$)$_6$CH$_2$CH═CH CH$_2$(CH$_2$)$_5$CH$_2$CH$_2$O ester +alcohol), 1.50 (m, CH$_2$CH$_2$O alcohol), 1.64 (m, CH$_2$CH$_2$O ester) 1.94 (m, CH$_2$CH═CHCH$_2$ ester +CH$_2$CH═CHCH$_2$ alcohol), 2.74 (s, CH$_3$SO$_3^-$ ester +CH$_3$SO$_3^-$ acid+CH$_3$SO$_3^-$ betaine glycine), 3.30 (s, (CH$_3$)$_3$ ester +(CH$_3$)$_3$ betaine glycine), 3.51 (t, CH$_2$CH$_2$O alcohol, $^3$J 6.7 Hz), 4.19 (t, CH$_2$CH$_2$O ester, $^3$J 6.8 Hz), 4.24 (s, CH$_2$CO betaine glycine), 4.32 (s, CH$_2$CO ester), 5.30 (m, CH$_2$CH═CHCH$_2$ ester +CH$_2$CH═CHCH$_2$ alcohol).

Composition of the mixture

| Method of treatment | a | b | c | d |
|---|---|---|---|---|
| A | 48 | 36 | 14 | 2 | a, b, c and d are expressed as a percentage by mass.

The reactional raw material is chromatographed on a column of silica gel (ethyl acetate-isopropanol-water (6.2:3:0.8 then 6:3:1)) to give about 100 g 9-octadecenyl betaine mesylate.

C$_{24}$H$_{49}$NO$_5$S; M=463.72 g/mol

Yellow viscous oil; yield: ≅85%

CCM: Rf 0.4 (ethyl acetate-isopropanol-water (6:3:1))

IR (Nujol) ν (cm$^{-1}$): 1755 (C═O); 1650 (C═C)

RMN $^{-1}$H(CDCl$_3$):

δ 0.83 (t, 3H, CH$_3$, $^3$J 6.8 Hz), 1.22 (sl, 22H, CH$_3$(CH$_2$)$_6$ CH$_2$CH═CH CH$_2$(CH$_2$)$_5$ CH$_2$CH$_2$O), 1.64 (m, 2H, CH$_2$CH$_2$O), 1.94 (m, 4H, CH$_2$CH═CH CH$_2$), 2.71 (s, 3H, CH$_3$SO$_3^-$), 3.30 (s, 9H, (CH$_3$)$_3$), 4.19 (t, 2H, CH$_2$CH$_2$O, $^3$J 6.8 Hz), 4.32 (s, 2H, CH$_2$CO), 5.31 (m, 2H, CH$_2$CH═CHCH$_2$).

RMN $^{13}$C (CDCl$_3$):

δ 14.21 (CH$_3$), 22.90, 25.89, 27.40, 28.49, 29.38, 29.52, 29.62, 29.73, 29.86, 29.91, 29.96, 32.13, 32.81 (CH$_2$ aliph.), 39.27 (CH$_3$SO$_3^-$), 54.09 ((CH$_3$)$_3$), 63.22 (CH$_2$CH$_2$O), 67.09 (CH$_2$CO), 129.93, 130.24 (CH$_2$CH═CHCH$_2$), 164.88 (CH$_2$CO).

EXAMPLE 3

Synthesis of Betainylaminooctadecane Mesylate and Preparation of a Corresponding Mixture A suspension of betaine glycine (25 g, 0.213 mole) in n-butanol (59 ml, 0.64 mole) was formed in the presence of methanesulphonic acid (22.56 g, 0.235 mole). The reactional mixture is brought to the reflux point of n-butanol at 140° C. The medium becomes homogeneous at the end of 3 to 4 hours' stirring. To the mixture cooled to ambient temperature is added dibutylamine (8.27 g, 0.064 mole) and the medium is stirred for about 15 minutes. Octadecylamine is then added (69 g, 0.256 mole), then the n-butanol is eliminated under reduced pressure. Aminolysis is carried out at 130° C. under reduced pressure (50 to 100 mbar). After 3 hours, the medium is cooled to ambient temperature. The reaction raw material obtained is washed with diethyl ether (1600 ml) until complete recovery of the residue. The precipitate obtained is then filtered on a Büchner and rinsed several times with the same solvent (2 □.200 ml). The product is dried in a vacuum and 98 g of a white powder having a surfactant composition according to the invention is eventually obtained.

RMN $^1$H of the mixture obtained (CDCL$_3$+CD$_3$OD, 1/1):

δ 0.90 (t, CH$_3$ amide+CH$_3$ amine salt, $^3$J 6.7 Hz), 1.29 (sl, (CH$_2$)$_{15}$CH$_3$ amide+(CH$_2$)$_{15}$CH$_3$ amine salt), 1.56 (m, CH$_2$CH$_2$NH amide), 1.67 (m, CH$_2$CH$_2$NH$_3^+$ amine salt), 2.78 (s, CH$_3$SO$_3^-$ amide+CH$_3$SO$_3^-$ amine salt+CH$_3$SO$_3^-$ betaine glycine), 2.91 (m, CH$_2$CH$_2$NH$_3^+$ amine salt), 3.26 (m, CH$_2$CH$_2$NH amide), 3.30 (s, (CH$_3$)$_3$ betaine glycine), 3.35 (s, (CH$_3$)$_3$ amide), 3.82 (s, CH$_2$CO betaine glycine), 4.10 (s, CH$_2$CO amide).

Composition of the Mixture

| Method of treatment | e | f | g | h |
|---|---|---|---|---|
| B | 58 | 35 | 0 | 10 | e, f, g and h are expressed as a percentage by mass of the mixture.

The product obtained by the method of treatment B is chromatographed on a column of silica gel (ethyl acetate-isopropanol-water (6:3:1 then 5:3:2) to give about 58 g betainylaminooctadecane mesylate.

C$_{24}$H$_{52}$N$_2$O$_4$S; M=464.75 g/mol

White solid; yield: ≅60%

CCM: Rf 0.5 (ethyl acetate-isopropanol-water (5:3:2))

IR (Nujol) ν (cm$^{-1}$): 1680 (Amide I); 1578 (Amide II)

RMN $^1$H (DMSO):

δ 0.86 (t, 3H, CH$_3$, $^3$J 6.8 Hz), 1.25 (sl, 30H, (CH$_2$)$_{15}$CH$_3$), 1.45 (m, 2H, CH$_2$CH$_2$NH), 2.37 (s, 3H, CH$_3$SO$_3^-$), 3.10 (m, 2H, CH$_2$CH$_2$NH), 3.21 (s, 9H, (CH$_3$)$_3$, 4.05 (s, 2H, CH$_2$CO), 8.64 (s, 1H, NH).

RMN $^{13}$C (DMSO):

δ 13.40 (CH$_3$) 21.63, 24.22, 26.01, 28.27, 28.59, 30.88 (CH$_2$ aliph.), 38.50, (CH$_2$NH), 39.42 (CH$_3$SO$_3$), 53.35 ((CH$_3$)$_3$), 64.24 (CH$_2$CO), 162.66 (CH$_2$CO).

EXAMPLE 4

Synthesis of Betainylaminooctadecenyl Mesylate and Preparation of The Corresponding Mixture A suspension of betaine glycine (25 g, 0.213 mole) in n-butanol (59 ml, 0.64 mole) was formed in the presence of methanesulphonic acid (22.56 g, 0.235 mole). The reactional mixture is brought to the reflux point of n-butanol at 140° C. The medium becomes homogeneous at the end of 3 to 4 hours' stirring. To the mixture cooled to ambient temperature is added oleic amine (68.5 g, 0.256 mole), then the n-butanol is eliminated under reduced pressure. Aminolysis is carried out at 130-140° C. under reduced pressure (50 to 100 mbar). After 3 hours, the medium is cooled to ambient temperature. The reactional raw material obtained (114 g) forms a surfactant composition according to the invention.

RMN $^1$H of the reactional raw material (CDCl$_3$):

δ 0.86 (t, CH$_3$ amide+CH$_3$ amine salt+CH$_3$ amine, $^3$J 6.7 Hz), 1.29 (sl, CH$_3$(CH$_2$)$_6$CH$_2$CH=CHCH$_2$(CH$_2$)$_5$CH$_2$CH$_2$N amide+amine salt+amine+CH$_2$CH$_2$NH$_2$ amine), 1.52 (m, CH$_2$CH$_2$NH amide), 1.61 (m, CH$_2$CH$_2$NH$_3$$^+$ amine salt), 1.98 (m, CH$_2$CH=CHCH$_2$ amide+amine salt+amine), 2.67 (t, CH$_2$CH$_2$NH$_2$ amine, $^3$J 6.8 Hz), 2.73 (s, CH$_3$SO$_3$$^-$ amide+CH$_3$SO$_3$$^-$amine salt+ CH$_3$SO$_3$$^-$ betaine glycine), 2.87 (m, CH$_2$CH$_2$NH$_3$$^+$ amine salt), 3.21 (m, CH$_2$CH$_2$NH amide), 3.27 (s, (CH$_3$)$_3$ betaine glycine), 3.31 (s, (CH$_3$)$_3$ amide), 3.77 (s, CH$_2$CO betaine glycine), 4.08 (s, CH$_2$CO amide), 5.30 (m, CH$_2$CH=CHCH$_2$ amide+amine salt+amine).

Composition of the Mixture

| Method of treatment | e | f | g | h |
|---|---|---|---|---|
| A | 56 | 31 | 8 | 5 | e, f, g and h are expressed as a percentage by mass of the mixture.

The reactional raw material is chromatographed on a column of silica gel (ethyl acetate-isopropanol-water (6:3:1 then 5:3:2)) in order to give about 64 g of betainylaminooctadecenyl mesylate.

C$_{24}$H$_{50}$N$_2$O$_4$S; M=462.74 g/mol
White solid; yield: ≈65%
CCM: Rf 0.52 (ethyl acetate-isopropanol-water (5:3:2))
IR (Nujol) ν (cm$^{-1}$): 1678 (Amide I); 1576 (Amide II) 1640 (C=C)

RMN $^1$H (DMSO):

δ 0.84 (t, 3H, CH$_3$, $^3$J 6.7 Hz), 1.23 (sl 22H, CH$_3$(CH$_2$)$_6$CH$_2$CH=CHCH$_2$(CH$_2$)$_5$CH$_2$CH$_2$NH), 1.40 (m, 2H, CH$_2$CH$_2$NH), 1.97 (m, 4H, CH$_2$CH=CHCH$_2$), 2.33 (s, 3H, CH$_3$SO$_3$$^-$), 3.08 (m, 2H, CH$_2$CH$_2$NH), 3.20 (s, 9H, (CH$_3$)$_3$), 4.07 (s, 2H, CH$_2$CO), 5.31 (m, 2H, CH$_2$CH=CHCH$_2$), 8.61 (s, 1H, NH).

RMN $^{13}$C (DMSO):

δ 14.08 (CH$_3$), 22.20, 26.43, 26.65, 26.69, 28.69, 28.73, 28.80, 28.92, 29.96, 29.17. 29.22, 31.38, 32.04 (CH$_2$ aliph.), 38.66 (CH$_2$NH), 39.78 (CH$_3$SO$_3$$^-$), 53.25 ((CH$_3$)$_3$), 63.86 (CH$_2$CO), 129.74, 129.75 (CH$_2$CH=CHCH$_2$), 163.19 (CH$_2$CO).

The physico-chemical properties of certain derivatives according to the invention are given below.

Measurement of Surface Tension and Critical Micellar Concentrations

The tensiometric measurements were carried out with a drop tensiometer operating by the method of the rising drop (TRACKER tensiometer, I.T. CONCEPT).

| Amphiphilic compounds | γcmc (mN/m) | CMC (M) |
|---|---|---|
| Esters | | |
| C$_{18:0}$ | 37.2 | $8 \cdot 10^{-4}$ |
| C$_{18:1}$ | 36.6 | $1 \cdot 10^{-4}$ |
| Amides | | |
| C$_{18:0}$ | 36.0 | $1.4 \cdot 10^{-4}$ |
| C$_{18:1}$ | 36.2 | $1.2 \cdot 10^{-4}$ |
| Examples of widely used Surfactants | | |
| APG (C$_{12}$) | 33.0 | $2.6 \cdot 10^{-4}$ |
| SDS (C$_{12}$) | 30.0 | $8 \cdot 10^{-3}$ |

Stability of Fatty Esters of the Betaine Glycine in an Aqueous Medium

Figure 1:
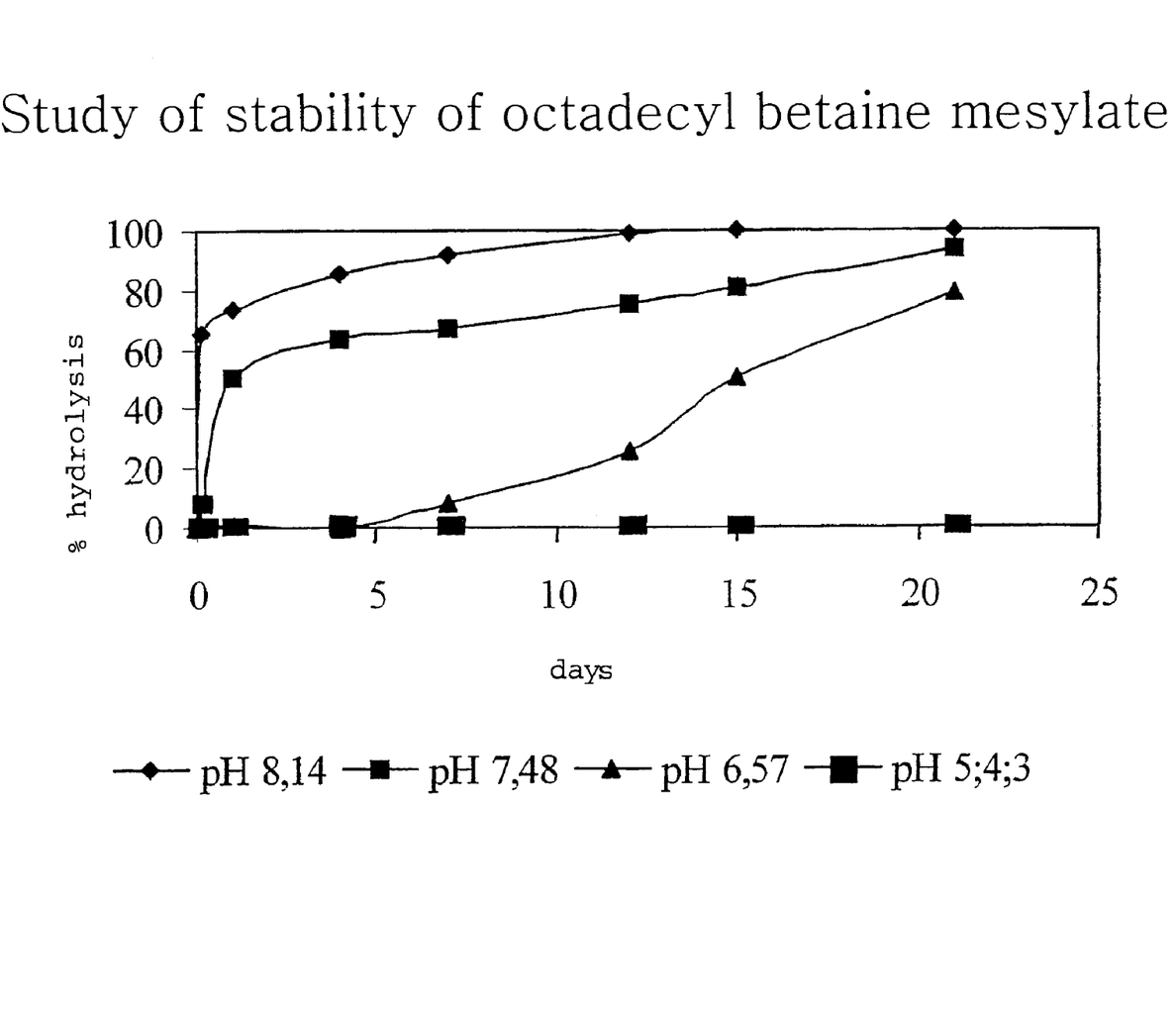
FIG. 1 shows the stability of actadecyl betaine mesylate in an aqueous buffer Solution at pH-values between 3 and 9.

The stability of octadecyl betaine mesylate is observed in an aqueous buffer solution whose pH-value is fixed to various values between 3 and 9. The initial concentration of surfactant in the buffer samples is $3.4 \cdot 10^{-2}$ Mole/l. The fatty alcohol released during the hydrolysis reaction is extracted by diethyl ether. After each extraction, the samples are centrifuged (10,000 rpm, 10 minutes) to "break" the emulsions formed. The etherised solution is then analysed by chromatography in a gaseous phase on an apolar column AT1 (polydimethylsiloxane) by using the n-dodecanol as an internal standard. The conditions applied are the following: injector at 320° C., detector at 330° C. and temperature gradient in the furnace; 200° C. (3 min.), 30° C./min (4 min.), 320° C. (5 min.). The only drawing shows the results obtained. Key to the drawing:

Title: Study of stability of octadecyl betaine mesylate; % hydrolyse- % hydrolysis; Jours-days

EXAMPLE 5

Formulation of an Acid Shampoo Using a Mixture with a Base of 9-octadecenyl Betaine Mesylate

| Mixture obtained in example 2 | 32 |
|---|---|
| Diethylanolamide of copra | 4 |
| Methylparaben | 0.1 |
| Propylparaben | 0.1 |
| Pale Morocco rose (rosa centifolia) | 0.5 |
| Distilled water | qsp 100 |
| Citric acid | qsp pH 5 |

EXAMPLE 6

Formulation of an Acid Shampoo Using a Mixture with a Base of Octadecyl Betaine Mesylate

| | |
|---|---|
| Mixture obtained in example 1, treatment C | 18.75 |
| Diethylanolamide of copra | 4 |
| Methylparaben | 0.1 |
| Propylparaben | 0.1 |
| Pale Morocco rose (*rosa centifolia*) | 0.5 |
| Distilled water | qsp 100 |
| Citric acid | qsp pH 5 |

Embodiments of methods described herein include:

Embodiment 1

A method of preparing a surfactant composition comprising: at least one compound of formula (1)

$$X^-(CH_3)_3N^+-CH_2-CO-Z-R \qquad (1)$$

and at least one compound selected from those with formulae (2), (3) and (4)

$$RZH \qquad (2)$$

$$XH \qquad (3)$$

$$X^-(CH_3)_3N^+-CH_2-CO-OH \qquad (4)$$

X being a sulphonate radical,

R being a monovalent radical of formula $C_{2n}H_{(2n-m)+1}$ containing 2n atoms of carbon and m double bonds, with $9 \leq n \leq 11$, $0 \leq m \leq 3$ if n=9 and $0 \leq m \leq 1$ if n>9, and Z being selected from an atom of oxygen and a —NH— group, a compound of formula XH being combined if necessary with at least one compound of formula $RNH_2$ in order to form at least one compound of formula $X^-RN^+H_3$, wherein betaine glycine is reacted with methanesulphonic acid and a compound of the formula ROH in the absence of other solvents, the molar ratio of methanesulphonic acid to betaine glycine being comprised between 2 and 3 and the molar ratio of the compound ROH to the betaine glycine being between 1 and 1.5.

Embodiment 2

The method according to Embodiment 1, wherein the reaction is carried out at a temperature of between 130 and 140° C. for 6 to 8 hours.

Embodiment 3

The method according to Embodiment 1, wherein the reaction is carried out under reduced pressure.

Embodiment 4.

The method according to Embodiment 1, wherein m=0 and the reactional mixture is treated with an organic solvent capable of dissolving preferably the compounds other than the $X^-(CH_3)_3N^+-CH_2-CO-O-R$ contained therein so as to obtain a precipitate enriched in $X^-(CH_3)_3N^+-CH_2-CO-O-R$.

Embodiment 5

The method according to Embodiment 4, wherein the organic solvent is selected from diethyl ether, ethanol and n-butanol.

Embodiment 6

A method of preparing a surfactant composition comprising:
at least one compound of formula (1)

$$X^-(CH_3)_3N^+-CH_2-CO-Z-R \qquad (1)$$

and at least one compound selected from those with formulae (2), (3) and (4)

$$RZH \qquad (2)$$

$$XH \qquad (3)$$

$$X^-(CH_3)_3N^+-CH_2-CO-OH \qquad (4)$$

X being a sulphonate radical,

R being a monovalent radical of formula $C_{2n}H_{(2n-m)+1}$ containing 2n atoms of carbon and m double bonds, with $9 \leq n \leq 11$, $0 \leq m \leq 3$ if n=9 and $0 \leq m \leq 1$ if n>9, and Z being selected from an atom of oxygen and a —NH— group, a compound of formula XH being combined if necessary with at least one compound of formula $RNH_2$ in order to form at least one compound of formula $X^-RN^+H_3$, wherein betaine glycine is reacted with methanesulphonic acid and n-butanol in the absence of other solvents, the molar ratio of the methanesulphonic acid to betaine glycine being between 1 and 1.3 and the molar ration of the n-butanol to the betaine glycine being between 2 and 4, in order to form water and the sulphonate of the n-butylic ester of betaine glycine, which is reacted, after elimination of the water and n-butanol, with the compound having the formula $RNH_2$, the molar ratio of this compound to betaine glycine being between 1 and 1.2.

Embodiment 7

The method according to Embodiment 6, wherein the reaction of the betaine glycine with the methanesulphonic acid and the n-butanol is carried out at a temperature of between 130 and 140° C., at the reflux of n-butanol, for 3 to 5 hours under atmospheric pressure so as to effect azeotropic elimination of water.

Embodiment 8

The method according to Embodiment 6, wherein, before the compound of formula $RNH_2$, is added a strong, encumbered organic base, in particular dibutylamine, the molar ratio of the base to the betaine glycine being between 0.1 and 0.4.

Embodiment 9

The method according to Embodiment 6, wherein m=0 and the reactional mixture is treated with an organic solvent capable of dissolving preferably the compound $RNH_3$ so as to obtain a precipitate enriched in $X^-(CH_3)_3N^+-CH_2-CO-NH-R$.

Embodiment 10

Method according to Embodiment 9, wherein the organic solvent is diethyl ether.

Embodiment 11

The method according to Embodiment 6, wherein the sulphonic acid is selected from methanesulphonic acid, paratoluenesulphonic acid and camphorsulphonic acid.

The invention claimed is:
1. A surfactant composition comprising:
at least one compound of formula (1)

$$X^-(CH_3)_3N^+\!-\!CH_2\!-\!CO\!-\!Z\!-\!R \qquad (1)$$

and at least one compound selected from those with formulae (2), (3) and (4)

$$RZH \qquad (2)$$

$$XH \qquad (3)$$

$$X^-(CH_3)_3N^+\!-\!CH_2\!-\!CO\!-\!OH \qquad (4)$$

X being a sulphonate radical,
R being a monovalent radical of formula $C_{2n}H_{2(2n-m)+1}$ containing 2n atoms of carbon and m double bonds, with $9 \leq n \leq 11$, $0 \leq m \leq 3$ if n=9 and $0 \leq m \leq 1$ if n>9, and
Z being selected from an atom of oxygen and a —NH— group,
a compound of formula XH being optionally combined with at least one compound of formula $RNH_2$ in order to form at least one compound of formula $X^-RN^+H_3$,
said composition excluding a compound of formula (1) where X is methylsulfonate, n is 9, m is 1 and Z is oxygen.

2. The composition according to claim 1, consisting essentially of at least one compound of formula (1) and at least one compound selected from those with formulae (2), (3) and (4).

3. The composition according to claim 1, wherein m=0 and the compounds forming the composition are as follows, in the percentages by weight indicated:

| | |
|---|---|
| $X^-(CH_3)_3N^+\!-\!CH_2\!-\!CO\!-\!O\!-\!R$ | 50 ± 10 |
| ROH | 19 ± 10 |
| XH | 23 ± 10 |
| $X^-(CH_3)_3N^+\!-\!CH_2\!-\!CO\!-\!OH$ | 0 to 18. |

4. The composition according to claim 1, wherein m=0 and the compounds forming the composition are the following, in the percentages by weight indicated:

| | |
|---|---|
| $X^-(CH_3)_3N^+\!-\!CH_2\!-\!CO\!-\!O\!-\!R$ | 72 ± 10 |
| ROH | 0 to 20 |
| XH | 0 to 18 |
| $X^-(CH_3)_3N^+\!-\!CH_2\!-\!CO\!-\!OH$ | 0 to 20. |

5. The composition according to claim 1, wherein m=0 and the compounds forming the composition are the following, in the percentages by weight indicated:

| | |
|---|---|
| $X^-(CH_3)_3N^+\!-\!CH_2\!-\!CO\!-\!O\!-\!R$ | 80 ± 10 |
| ROH | 20 ± 10. |

6. The composition according to claim 1, wherein m=0 and the compounds forming the composition are the following, in the percentages by weight indicated:

| | |
|---|---|
| $X^-(CH_3)_3N^+\!-\!CH_2\!-\!CO\!-\!O\!-\!R$ | 70 ± 10 |
| ROH | 26 ± 10 |
| XH | 0 to 14. |

7. The composition according to claim 1, wherein m >0 and the compounds forming the composition are the following, in the percentages by weight indicated:

| | |
|---|---|
| $X^-(CH_3)_3N^+\!-\!CH_2\!-\!CO\!-\!O\!-\!R$ | 48 ± 10 |
| ROH | 36 ± 10 |
| XH | 14 ± 10 |
| $X^-(CH_3)_3N^+\!-\!CH_2\!-\!CO\!-\!OH$ | 0 to 12. |

8. The composition according to claim 1, wherein m=0 and the compounds forming the composition are the following, in the percentages by weight indicated:

| | |
|---|---|
| $X^-(CH_3)_3N^+\!-\!CH_2\!-\!CO\!-\!NH\!-\!R$ | 58 ± 10 |
| $X^-RN^+H_3$ | 35 ± 10 |
| $X^-(CH_3)_3N^+\!-\!CH_2\!-\!CO\!-\!OH$ | 0 to 20. |

9. The composition according to claim 1, wherein m >0 and the compounds forming the composition are the following, in the percentages by weight indicated:

| | |
|---|---|
| $X^-(CH_3)_3N^+\!-\!CH_2\!-\!CO\!-\!NH\!-\!R$ | 56 ± 10 |
| $X^-RN^+H_3$ | 31 ± 10 |
| $RNH_2$ | 0 to 18 |
| $X^-(CH_3)_3N^+\!-\!CH_2\!-\!CO\!-\!OH$ | 0 to 15. |

10. The composition according to claim 1, wherein X is selected from the radicals methane sulphonate, paratoluene sulphonate and camphosulphonate.

11. A method of preparing a composition of claim 1, wherein betaine glycine is reacted with methanesulphonic acid and a compound of the formula ROH in the absence of other solvents, the molar ratio of methanesulphonic acid to betaine glycine being comprised between 2 and 3 and the molar ratio of the compound ROH to the betaine glycine being between 1 and 1.5.

12. A method of preparing a composition of to claim 1, wherein betaine glycine is reacted with methanesulphonic acid and n-butanol in the absence of other solvents, the molar ratio of the methanesulphonic acid to betaine glycine being between 1 and 1.3 and the molar ration of the n-butanol to the betaine glycine being between 2 and 4, in order to form water and the sulphonate of the n-butylic ester of betaine glycine, which is reacted, after elimination of the water and n-butanol, with the compound having the formula $RNH_2$, the molar ratio of this compound to betaine glycine being between 1 and 1.2.

13. A cosmetic formulation comprising the composition of claim 1.

14. The cosmetic formulation according to claim 13, further comprising at least one excipient selected from thickeners, texturisers, conditioning agents, softeners, complexing agents, perfumes, pearlising agents, preservatives, acidifiers and purified water.

15. The cosmetic formulation according to claim 14, comprising at least one diethanolamide of a fatty acid.

16. The cosmetic formulation according to claim 15, comprising up to 10% by weight of the total weight of the formulation of one or more diethanolamides of fatty acids.

17. A composition according to claim 1, comprising at least one compound of formula (1) and at least one compound of formula (2).

18. A composition according to claim 1, comprising at least one compound of formula (1) and at least one compound of formula (3).

19. A composition according to claim 1, comprising at least one compound of formula (1) and at least one compound of formula (4).

20. A composition according to claim 1, comprising at least one compound of formula (1) and at least one compound of the formula $X^-RN^{+H}{}_3$.

21. The method according to claim 11, wherein the reaction is carried out at a temperature of between 130 and 140° C. for 6 to 8 hours.

* * * * *